United States Patent [19]

Naiki et al.

[11] Patent Number: 5,532,271
[45] Date of Patent: Jul. 2, 1996

[54] FURANONE DERIVATIVES FOR THE SUPPRESSION OR TREATMENT OF AUTOIMMUNE DISEASES

[75] Inventors: Mitsuru Naiki; Yuichi Takeoka; Seishi Suehiro, all of Hyogo, Japan

[73] Assignee: Nippon Zoki Pharmaceutical Co., Ltd., Osaka, Japan

[21] Appl. No.: 301,398

[22] Filed: Sep. 8, 1994

Related U.S. Application Data

[62] Division of Ser. No. 950,563, Sep. 25, 1992, Pat. No. 5,376,682.

[30] Foreign Application Priority Data

Sep. 26, 1991 [JP] Japan .................................. 3-276543

[51] Int. Cl.⁶ .................................................. A61K 31/34
[52] U.S. Cl. .................................................... 514/473
[58] Field of Search ................................. 514/473, 474

[56] References Cited

U.S. PATENT DOCUMENTS 5,045,564   9/1991   Lee .......................................... 514/471

OTHER PUBLICATIONS

Leibovitz et al, *Chemical Abstracts,* vol. 94, No. 19, abstract 155368v, May 1981, p. 531.

*Primary Examiner*—Marianne M. Cintins
*Assistant Examiner*—William R. A. Jarvis
*Attorney, Agent, or Firm*—Armstrong, Westerman, Hattori, McLeland & Naughton

[57] ABSTRACT

The present invention relates to a method for preventing or treating autoimmune diseases in a mammal which comprises administering to the mammal an effective amount of at least one furanone derivative of the formula (I):

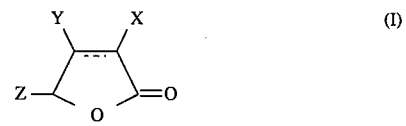

wherein X is hydrogen, hydroxy, a lower alkyl group or a lower alkylene group; Y is hydrogen, hydroxy or a lower alkyl group; Z is hydrogen, a lower alkyl group or a lower hydroxyalkyl group; and the broken line represents the presence or absence of a second bond; or a pharmaceutically acceptable salt thereof.

5 Claims, 8 Drawing Sheets

FURANONE DERIVATIVES FOR THE SUPPRESSION OR TREATMENT OF AUTOIMMUNE DISEASES

This is a division of application Ser. No. 07/950,563 filed Sep. 25, 1992, now U.S. Pat. No. 5,376,682.

BACKGROUND OF THE INVENTION

The present invention relates to a method for preventing or treating autoimmune diseases in a mammal which comprises administering the mammal an effective amount of at least one furanone derivative or a pharmaceutically acceptable salt thereof.

The disease caused by autoantibody inducing tissue damage is referred as an autoimmune disease, for example, collagen disease such as systemic lupus erythematosus or rheumatoid arthritis, demyelinating disease such as multiple sclerosis or postvaccinal encephalomyelitis, autoimmune hemolytic anemia, Hashimoto's disease and the like.

Adrenocorticotropic hormone, immunosuppressant and anti-inflammatory are generally used as a therapeutic drug for autoimmune diseases. However, an autoimmune disease has not been made so clear that there is no specific drug at present.

As a result of investigations for allergy and immunity involving autoimmune diseases, the present inventors have found that furanone derivatives of the present invention have excellent immunosuppressive effect for preventing or treating autoimmune diseases.

An object of the present invention is to provide a method for preventing or treating autoimmune diseases in a mammal which comprises administering the mammal an effective amount of at least one furanone derivative or a pharmaceutically acceptable salt thereof.

DETAILED DESCRIPTION OF THE INVENTION

The present invention relates to a method for preventing or treating autoimmune diseases in a mammal which comprises administering the mammal an effective amount of at least one furanone derivative of the following formula (I) or a pharmaceutically acceptable salt thereof:

(I)

In the formula (I), X represents hydrogen, hydroxy, a lower alkyl group, preferably a straight or branched alkyl group having 1 to 3 carbon atoms such as methyl, ethyl, propyl or isopropyl, or a lower alkylene group, preferably a alkylene group having 1 to 3 carbon atoms such as methylene, ethylene or propylene; Y represents hydrogen, hydroxy or a lower alkyl group, preferably a straight or branched alkyl group having 1 to 3 carbon atoms such as methyl, ethyl, propyl or isopropyl; Z represents hydrogen, a lower alkyl group, preferably a straight or branched alkyl group having 1 to 3 carbon atoms such as methyl, ethyl, propyl or isopropyl, or a lower hydroxyalkyl group, preferably a straight or branched hydroxyalkyl group having 1 to 3 carbon atoms such as hydroxymethyl, hydroxyethyl, hydroxypropyl or hydroxyisopropyl; and the broken line represents the presence or absence of a second bond.

Preferred compounds of the present invention are indicated as follows:

| No. | Name |
|---|---|
| 1 | 2(5H)-furanone |
| 2 | 5-hydroxymethyl-2(5H)-furanone |
| 3 | dihydro-3-methyl-2(3H)-furanone |
| 4 | dihydro-3-methylene-2(3H)-furanone |
| 5 | dihydro-4-hydroxy-2(3H)-furanone |
| 6 | dihydro-3-hydroxy-5-hydroxymethyl-2(3H)-furanone |
| 7 | dihydro-5-methyl-2(3H)-furanone |
| 8 | 4-methyl-2(5H)-furanone |

The said furanone derivatives of the present invention are known compounds. For example, they are disclosed in the following documents.

(1) J. Synthetic Org. Chem. Japan, .44(2), 127 (1986)

(2) Tetrahedron Letters, 28(20), 2299 (1987)

(3) J. Org. Chem., 46, 2299 (1981)

The furanone derivatives of the present invention include pharmaceutically acceptable salts of the compounds having formula (I) above, for example, salts as acid addition with an acid such as hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, glyconic acid, lactic acid, malonic acid, fumaric acid, anthranilic acid, benzoic acid, cinnamic acid, p-toluenesulfonic acid, naphthalenesulfonic acid or sulfanilic acid, salts with alkali metal such as sodium or potassium, salts with alkaline-earth metal such as calcium, magnesium or barium, or salts with other metals such as aluminum.

The furanone derivatives of this invention may also include their metal complexes, for example, complexes with zinc, nickel, cobalt, copper, iron etc.

These salts and metal complexes can be produced from free furanone derivatives in the usual way or can be interchanged with each other.

When stereoisomers such as cis-trans isomers, optical isomers and conformational isomers exist in the compounds of the invention, the present invention includes any of the isomers.

The following descriptions serve to illustrative pharmacological studies of the compounds of the present invention.

(1) Inhibitory effect on mixed lymphocyte culture reaction (MLR)

Responding cells ($5\times10^5$ cells) isolated from C57BL/6 mouse (H-$2^b$) were cultured with irradiated stimulation cells ($5\times10^5$ cells) from BALB/c mouse (H-$2^d$) in RPMI-1640 medium supplemented with 10% fetal bovine serum, or also responding cells ($5\times10^5$ cells) isolated from BALB/c mouse (H-$2^d$) were cultured with mitomycin-C treated stimulation cells ($5\times10^5$ cells) from C57BL/6 mouse (H-$2^b$). The test compound diluted with the medium was added into the culture. The cells were cultured at 37° C. under the condition of 5% $CO_2$- 95% air and 100% humidity for 72 hrs, labeled with $^3$H-thymidine (18.5 KBq) for last 6 hrs and finally harvested on glassfiber filters. The incorporation of $^3$H-thymidine was measured by a liquid scintillation counter. The results are shown in Tables 1 to 6.

TABLE 1

| Compound 1 (μg/ml) | Radioactivity (mean cpm) | Inhibition (%) |
|---|---|---|
| 0 | 23999 | 0 |
| 5 | 23893 | 0.4 |
| 10 | 14095 | 41.3 |
| 25 | 877 | 96.3 |
| 50 | 282 | 98.8 |
| 100 | 27 | 99.9 |

TABLE 2

| Compound 2 (μg/ml) | Radioactivity (mean cpm) | Inhibition (%) |
|---|---|---|
| 0 | 51053 | 0 |
| 1 | 52480 | −2.8 |
| 10 | 46736 | 8.5 |
| 100 | 23013 | 54.9 |
| 1000 | 37 | 99.9 |

TABLE 3

| Compound 3 (μg/ml) | Radioactivity (mean cpm) | Inhibition (%) |
|---|---|---|
| 0 | 51053 | 0 |
| 1 | 49673 | 2.7 |
| 10 | 43701 | 14.4 |
| 100 | 32182 | 37.0 |
| 1000 | 302 | 99.4 |

TABLE 4

| Compound 4 (μg/ml) | Radioactivity (mean cpm) | Inhibition (%) |
|---|---|---|
| 0 | 51053 | 0 |
| 1 | 39011 | 23.6 |
| 10 | 22538 | 55.9 |
| 100 | 65 | 99.9 |
| 1000 | 71 | 99.9 |

TABLE 5

| Compound 5 (μg/ml) | Radioactivity (mean cpm) | Inhibition (%) |
|---|---|---|
| 0 | 16767 | 0 |
| 1 | 17181 | −2.5 |
| 10 | 20766 | −23.9 |
| 100 | 12207 | 27.2 |
| 1000 | 42 | 99.8 |

TABLE 6

| Compound 6 (μg/ml) | Radioactivity (mean cpm) | Inhibition (%) |
|---|---|---|
| 0 | 16767 | 0 |
| 1 | 15598 | 7.0 |
| 10 | 16208 | 3.3 |
| 100 | 6447 | 61.6 |
| 1000 | 31 | 99.8 |

(2) Suppressive effect on experimental allergic encephalomyelitis (EAE)

a) Clinical assessment

EAE was induced by the established method [M. Naiki et al., Int. J. Immunopharmac. 13(2/3), 235–243 (1991)]. Synthetic peptide (MB68–84) corresponding to the encepalitogenic determinant of guinia pig meylin basic protein (MBP), residues 68–84, was dissolved in phosphate-buffered saline (0.2 mg/ml), and was emulsified in an equal volume of complete adjuvant containing 2.5 mg/ml of heat inactivated tuberculosis. Female Lewis rats (body weight 160–170 g) were sensitized by inoculation with 0.1 ml of the emulsion in the left hind foot pad.

The rats were injected daily intraperitoneally with the test compound which was dissolved in saline and clinical scores of the disease were assessed after immunization. A clinical score was used to grade animals on scores of from 0 to 5 as follows: grade 0=normal; grade 1=inactive or tail weakness; grade 2=weakness of hind legs or mild ataxia; grade 3=hind legs paralysis of severe ataxia; grade 4=severe hind legs paralysis; grade 5=severe four legs paralysis or dying.

The suppressive effects of the compounds of the present invention on the expression of EAE are shown in FIGS. 1 to 6.

b) Histological assessment

The rats were injected daily with the test compound during from day 0 to day 13 after immunization of MB68–84. The rats were perfused through the heart with a fixative and the central nervous system was removed at day 14 after immunization. For assessment of perivascular infiltration, one section of brain and three sections of lumber vertebrae were embedded in paraffin, cut at time thickness of 5 μm, stained with hematoxylin/eosin, and observed by using the optical microscope.

Inflammation of leptomeninges and choroid plexus was assessed according to 6 grades as follows: 0=no abnormality; 1=few scattered inflammation; 2=slight inflammation; 3=middle inflammation; 4=many inflammation; 5=severe and dense inflammation.

Perivascular inflammation (cuffing) was assessed according to 6 grade as follows: 0=no abnormality; 1=few scattered cuffs; 2=perivascular cuffs involving about 25% of blood vessels; 3=perivascular cuffs involving about 50% of blood vessels; 4=perivascular cuffs involving about 75% of blood vessels; 5=nearly all vessels involved.

The tissue infiltration by inflammatory cells was assessed according to 6 grades as follows: 0=no cells, 1 =few scattered cells invading neural parechyma; 2=invasion of cells into parechyma from about 25% of perivascular cuffs; 3=invasion of cells into parechyma from about 50% of perivascular cuffs; 4=invasion of cells into parechyma from about 75% of perivascular cuffs; 5= large confluent areas of involvement from nearly all perivascular cuffs.

The inhibitory effect of the compounds of the present invention on histological change of EAE is indicated in Table 1. The result is expressed as a mean value ±standard error of nine rats in each groups. The Mann-Whitony's U-test was used for analysis. Asterisks indicate significance in comparison with control group (*: $p<0.01$, **: $p<0.001$).

TABLE 7

| | Control (Saline) | Compound 1 (100 mg/ml) |
|---|---|---|
| 1) Inflammation of leptomeninges and choroid plexus | 3.9 ± 0.4 | 1.9 ± 0.6* |
| 2) Perivascular inflammation | 4.0 ± 0.3 | 1.3 ± 0.5** |
| 3) Tissue infiltration by inflammatory cells | 3.9 ± 0.3 | 1.0 ± 0.4** | c) Number of cells in inguinal lymph node

Inguinal lymph nodes were removed from Lewis rats, which were injected with the test compounds daily from day 0 to day 13. At day 14 after immunization of MB68–84, single cell suspensions were prepared with mesh and viable cells were selectively counted by trypan blue staining method. An example of results is shown in Table 2. Asterisk indicates significance in comparison with control group (*: $p<0.05$).

TABLE 8

|  | Control (Saline) | Compound 1 (100 mg/ml) |
| --- | --- | --- |
| Number of cells in inguinal lymph node ($\times 10^7$) | 7.1 ± 1.1 | 3.9 ± 0.7* |

(3) Effect on type II collagen-induced arthritis

Bovine type II collagen dissolved in 0.01M acetic acid (2 mg/ml) was emulsified in an equal volume of Freund's incomplete adjuvant. Female Lewis rats were sensitized by inoculation with 0.5 ml of the emulsion at several sites on the back. The rats were challenged with 0.2 ml of the emulsion into the base of tail at day 7 after immunization. Clinical scores of arthritis on four legs every fourth day by using 4 grades (from 0 to 3) were assessed. The test compound dissolved in saline was daily administered intraperitoneally from day 1 to day 21 after immunization to evaluate the inhibitory effect. To evaluate the therapeutic effect, the test compound was also administered from day 15 to day 21.

The result was expressed as a mean value ±standard error of seven rats in each groups. The Mann-Whitony's U-test was used for analysis. Asterisks indicate significance in comparison with control group (*: $p<0.05$). The inhibitory effect of the compound of the present invention on type II collagen-induced arthritis is shown in FIG. 7, and the therapeutic effect is also shown in FIG. 8.

As indicated in the Tables 1 to 6, the compounds of the present invention show significant inhibitory effects on mixed lymphocyte culture reaction (MLR), which surely demonstrate that the compounds have excellent immunosuppressive activity.

Experimental allergic encephalomyelitis (EAE) has been used as a model for autoimmune disease, especially demyelinating disease such as multiple sclerosis or postvaccinal encephalomyelitis. As shown in the FIGS. 1 to 6, the compounds of the present invention significantly suppressed the clinical symptoms of EAE. Additionally, in histological assessment, the infiltration of inflammatory cells to the central nervous system, which was observed at day 14 after immunization, i.e. when clinical symptoms of EAE was expressed most severely, was apparently reduced by the administration of the compound of this invention.

Figure 1:
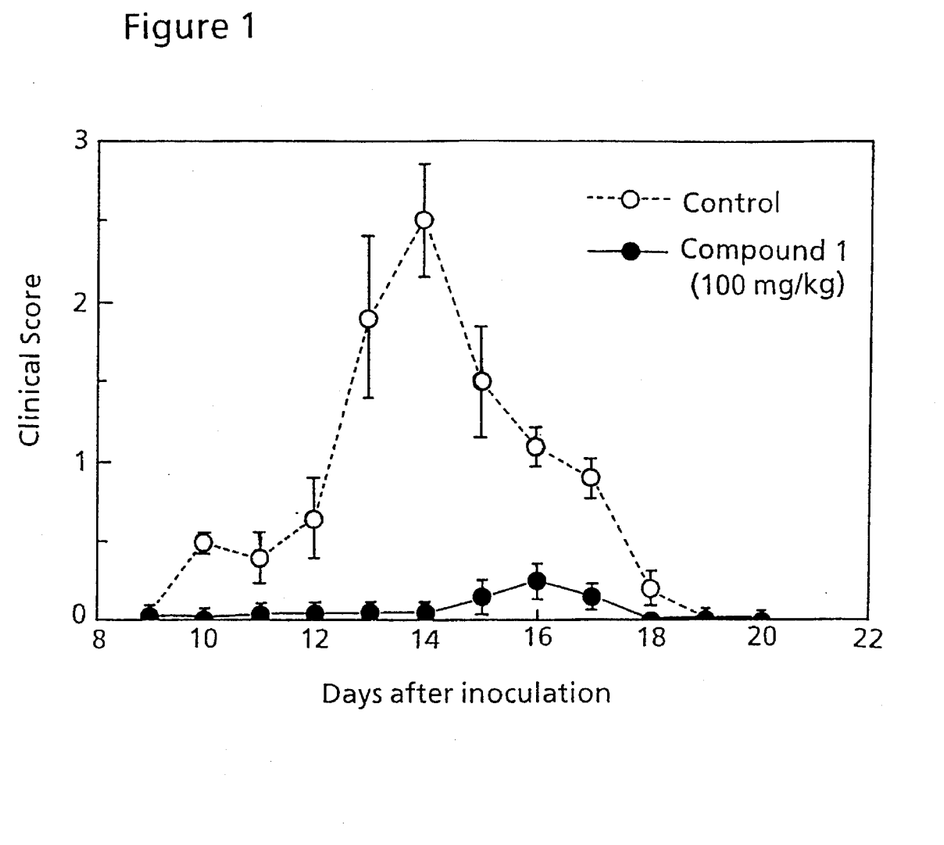
FIGS. 1, 2, 3, 4, 5, and 6 show the clinical assessment of therapeutic effect of the compounds of the present invention on encephalomyelitis (EAE).
Figure 2:
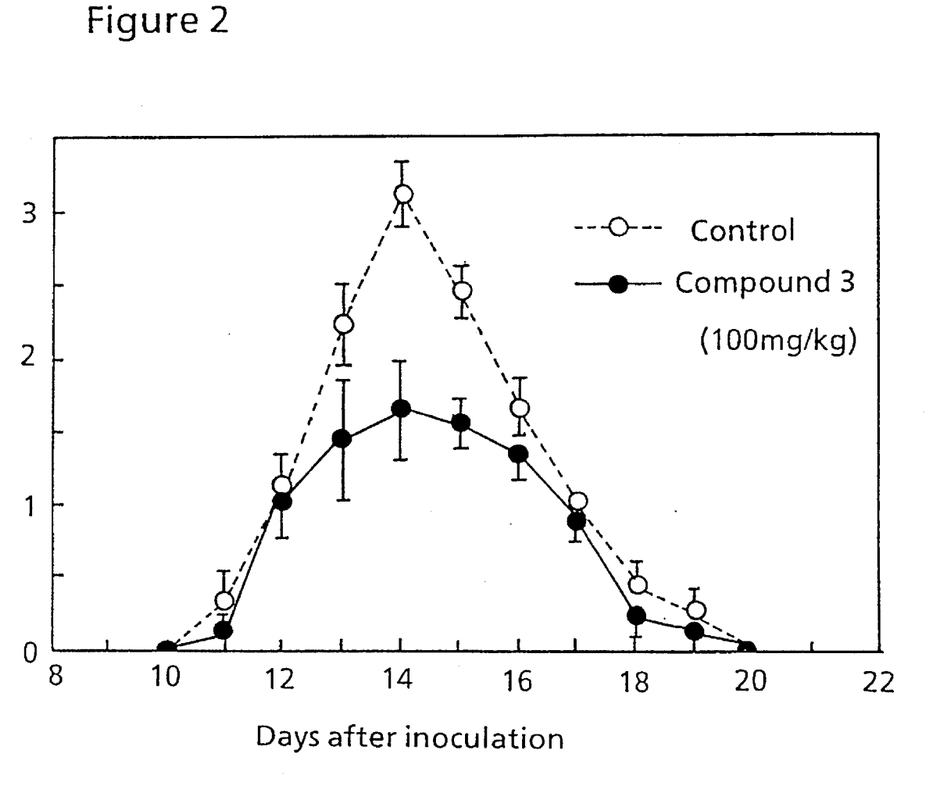
Figure 3:
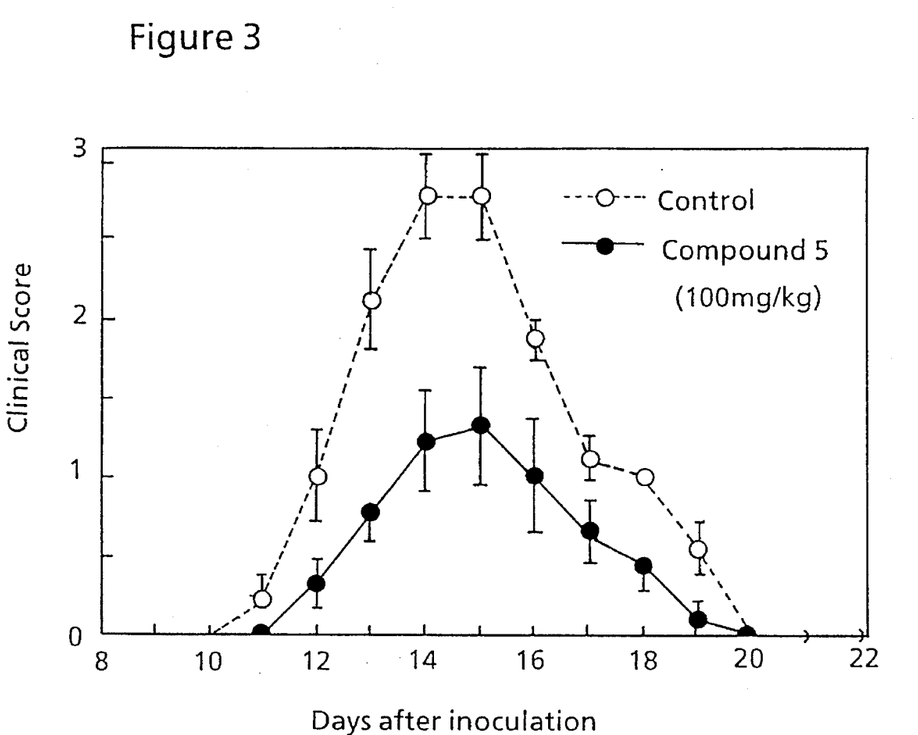
Figure 4:
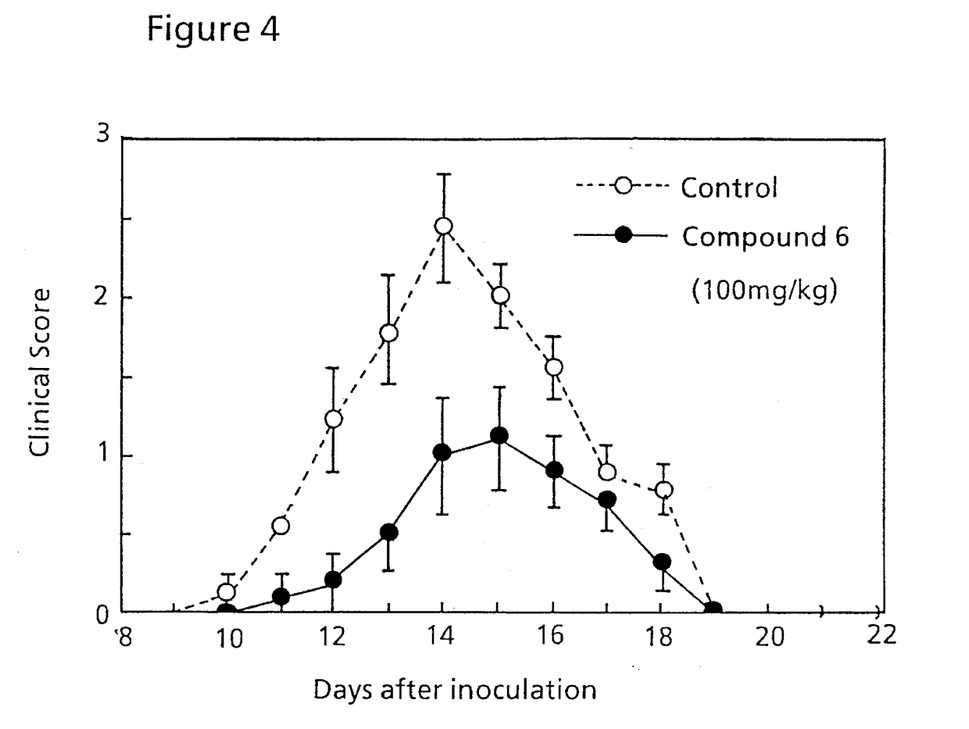
Figure 5:
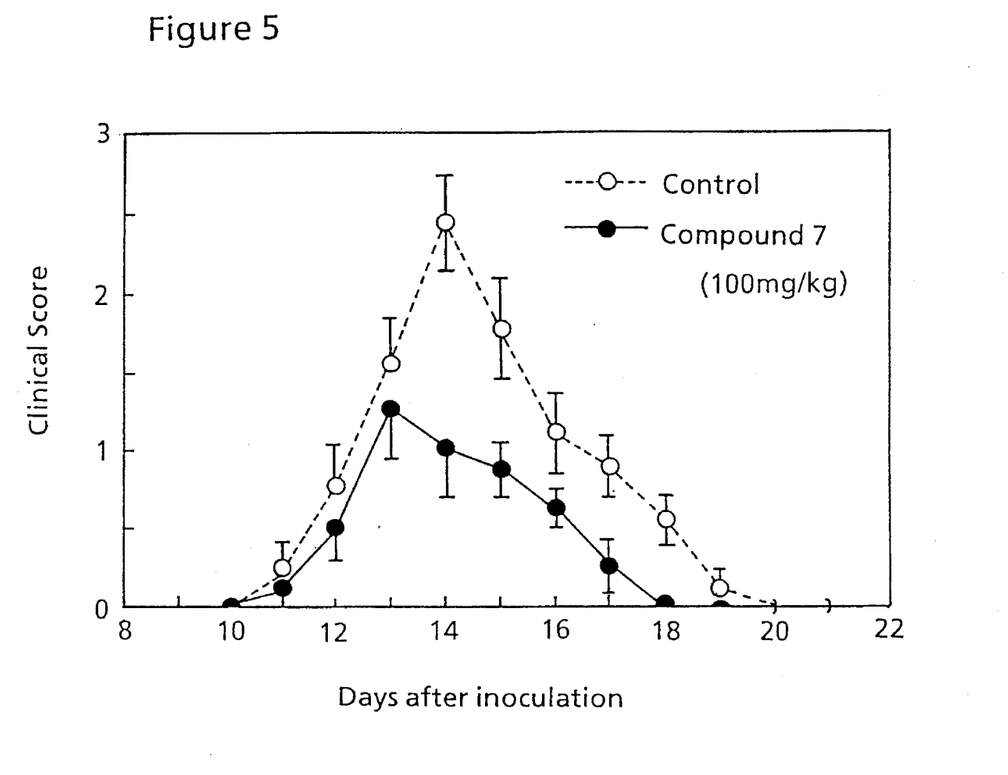
Figure 6:
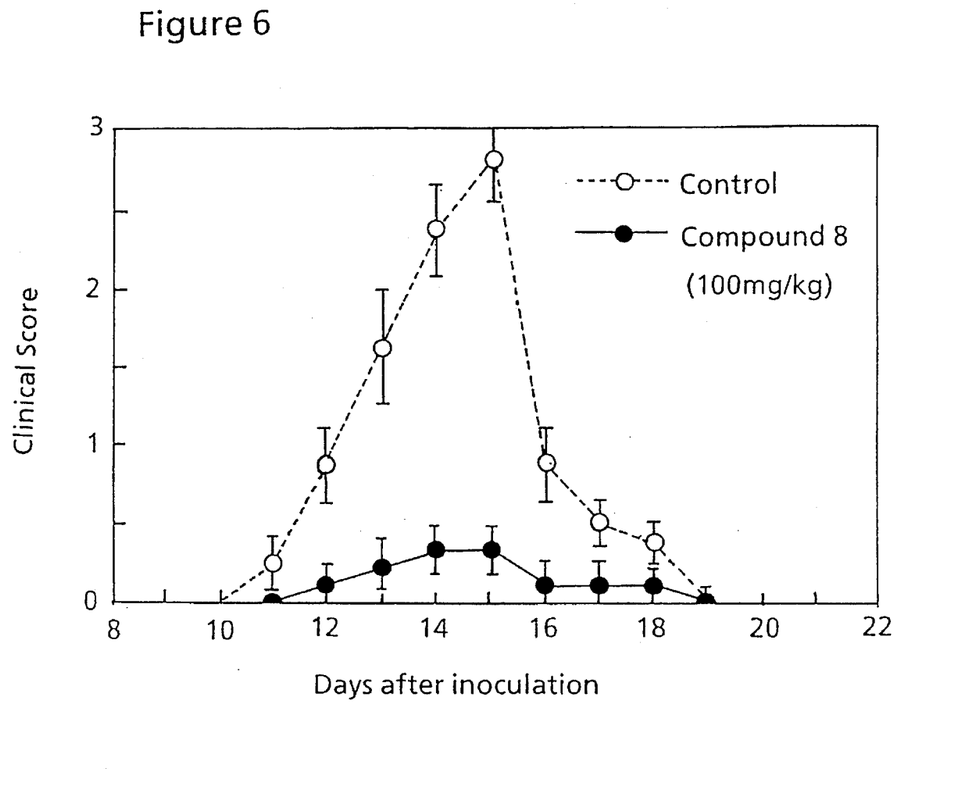
Figure 7:
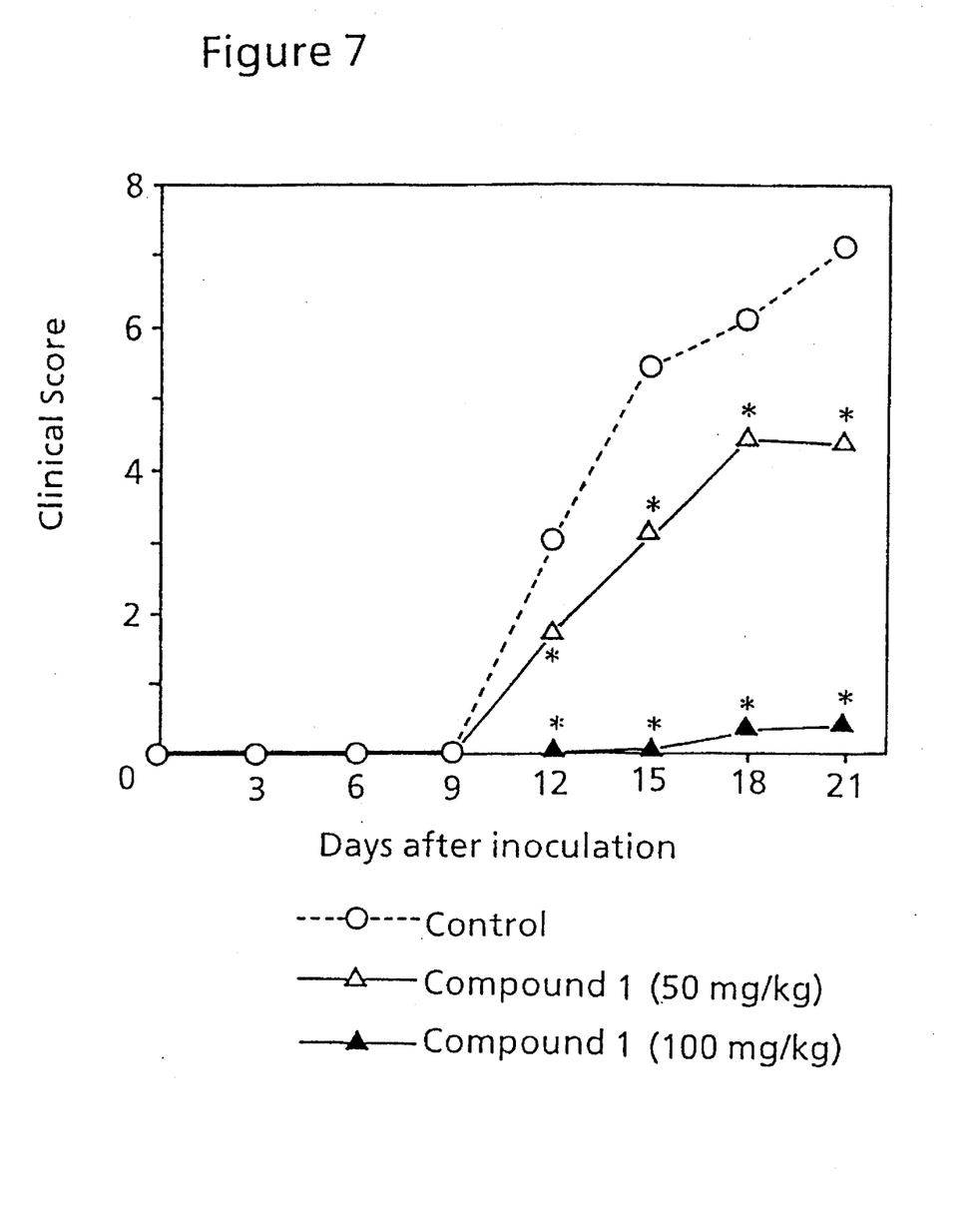
FIG. 7 shows the inhibitory effect of the present compound on type II collagen-induced arthritis, and also
Figure 8:
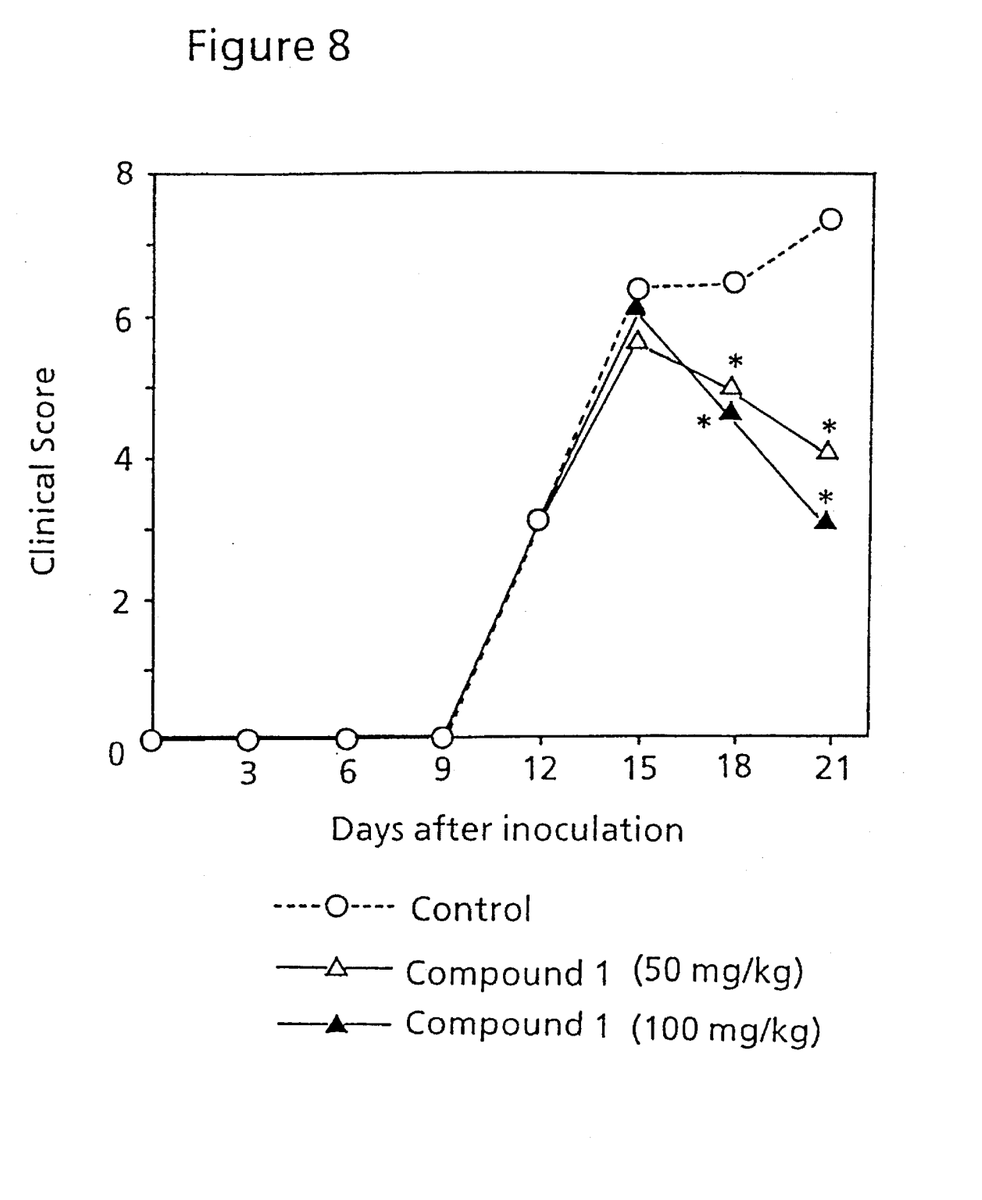
FIG. 8 shows the therapeutic effect.

Also as shown in the FIGS. 7 and 8, the compounds of the present invention have inhibitory and therapeutic effects on type II collagen-induced arthritis, which is one of the principal animal models for human rheumatism.

The compounds of this invention decrease the number of cells in inguinal lymph node on EAE (Table 8), and show the inhibitory effect on MLR (Tables 1 to 6). These results suggest that the effect on the autoimmune diseases of the compounds of the present invention may depend upon their immunosuppressive activities.

As shown by the results of the pharmacological tests, the compounds of the present invention are very useful as drugs for treatment and prevention of autoimmune diseases, for example, collagen diseases such as systemic lupus erythematosus and rheumatoid arthritis, demyelinating diseases such as multiple sclerosis and pestvaccinal encephalomyelitis, autoimmune hemolytic anemia, Hashimoto's disease and the like.

The compounds of the present invention can be made into pharmaceutical compositions by combination with appropriate medicinal carriers or diluents, and can be formulated into preparations in solid, semisolid, liquid or gaseous form in usual ways for oral or parenteral administrations.

In pharmaceutical dosage forms, the compounds of the present invention can be used in the form of their pharmaceutically acceptable salts, and also can be used alone or in appropriate association, as well as in combination with other pharmaceutically active components.

In case of oral preparations, the compounds can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the invention can be made into a suppository by mixing with a a variety of bases, e.g. fatty and oily base such as cacao butter, emulsifying base or water-soluble base such as macrogol.

The compounds of the present invention can be formulated into a preparations for injections by dissolving, suspending or emulsifying in aqueous or non-aqueous solvent, such as distilled water for injection, physiologically saline solution, vegetable oil, synthetic aliphatic acid glycerides, esters of higher aliphatic acid or propylene glycol.

Furthermore, according to a kind of disease or patient, the compounds of the invention can be formulated into other preparations suitable for treatment of the disease, such as inhalation, aerosol, collyrium, ointment and cataplasma.

The desirable dose of the compounds of the present invention varies with the subject, form of the drug, method and period of administration. However, in order to obtain desirable effects, generally it is recommended to administer orally 1 to 5,000 mg, preferably 5 to 1,000 mg daily.

In case of parenteral administrations e.g. injections, doses of the compounds in the order of one tenth to one third of the above dose are preferable as daily doses.

Prescriptions of the pharmaceutical compositions are shown below as examples which contain the compounds of the present invention as active ingredients. These examples, however, do not limit time present invention.

| Prescription example 1 (tablet) | |
| --- | --- |
| Component | Content in a tablet (mg) |
| compound of this invention | 50 |
| lactose | 130 |
| corn starch | 40 |
| magnesium stearate | 10 |
| Total | 230 mg |

| Prescription example 2 (injection) | |
| --- | --- |
| Component | Content in an ampule (mg) |
| compound of this invention | 10 |
| sodium chloride | proper amount |
| distilled water for injection | proper amount |
| Total | 1 ml |

What is claimed is:

1. A method for suppressing or treating autoimmune diseases in a mammal which comprises administering to the mammal an effective amount of at least one furanone compound of the formula wherein X is hydrogen, hydroxy, a lower alkyl group or a lower alkylene group; Y is hydrogen, hydroxy or a lower alkyl group having 1–3 carbons, Z is hydrogen, a lower alkyl group or a hydroxy lower alkyl group; and the broken line represents the presence or absence of a second bond;
or a pharmaceutically acceptable salt thereof.

2. A method according to claim 1, wherein the furanone compound is unsaturated and the broken line represents the presence of a second bond.

3. A method according to claim 2, wherein the furanone compound is 2(5H)-furanone, 5-hydroxymethyl-2(5H)-furanone or 4-methyl-2(5H)-furanone.

4. A method according to claim 1, wherein the furanone compound is saturated and the broken line represents the absence of a second bond.

5. A method according to claim 4, wherein the furanone compound is dihydro-3-methyl-2(3H)-furanone, dihydro-3-methylene-2(3H)-furanone, dihydro-4-hydroxy-2(3H)-furanone, dihydro-3-hydroxy-5-hydroxymethyl-2(3H)-furanone or dihydro-5-methyl-2(3H)-furanone.

* * * * *